(12) United States Patent
Pandev et al.

(10) Patent No.: US 10,490,462 B2
(45) Date of Patent: Nov. 26, 2019

(54) METROLOGY SYSTEMS AND METHODS FOR PROCESS CONTROL

(71) Applicant: KLA-Tencor Corporation, Milpitas, CA (US)

(72) Inventors: Stilian Ivanov Pandev, Santa Clara, CA (US); Dzmitry Sanko, Vallejo, CA (US); Andrei V. Shchegrov, Campbell, CA (US)

(73) Assignee: KLA Tencor Corporation, Milpitas, CA (US)

( * ) Notice: Subject to any disclaimer, the term of this patent is extended or adjusted under 35 U.S.C. 154(b) by 0 days.

(21) Appl. No.: 15/782,542

(22) Filed: Oct. 12, 2017

(65) Prior Publication Data

US 2018/0108578 A1 Apr. 19, 2018

Related U.S. Application Data

(60) Provisional application No. 62/407,658, filed on Oct. 13, 2016.

(51) Int. Cl.
*G01N 21/25* (2006.01)
*H01L 21/66* (2006.01)
(Continued)

(52) U.S. Cl.
CPC .......... *H01L 22/12* (2013.01); *G01B 11/0625* (2013.01); *G01B 11/24* (2013.01);
(Continued)

(58) Field of Classification Search
CPC .. G01B 11/0625; G01B 11/24; G01N 21/255; G01N 21/9503; G03F 7/705; G03F 7/70625; H01L 22/26
(Continued)

(56) References Cited

U.S. PATENT DOCUMENTS

| 5,608,526 | A | | 3/1997 | Piwonka-Corle et al. |
| 5,665,214 | A | * | 9/1997 | Iturralde ............. C23C 14/0042 |
| | | | | 118/690 |

(Continued)

FOREIGN PATENT DOCUMENTS

| JP | 2013-042114 A | 2/2013 |
| JP | 2015-532544 A | 11/2015 |

OTHER PUBLICATIONS

International Search Report dated Jan. 25, 2018, for PCT Application No. PCT/US20171056406 filed on Oct. 12, 2017 by KLA-Tencor Corporation, 3 pages.

*Primary Examiner* — Isiaka O Akanbi
(74) *Attorney, Agent, or Firm* — Spano Law Group; Joseph S. Spano

(57) ABSTRACT

Methods and systems for estimating values of parameters of interest based on repeated measurements of a wafer during a process interval are presented herein. In one aspect, one or more optical metrology subsystems are integrated with a process tool, such as an etch tool or a deposition tool. Values of one or more parameters of interest measured while the wafer is being processed are used to control the process itself. The measurements are performed quickly and with sufficient accuracy to enable yield improvement of a semiconductor fabrication process flow. In one aspect, values of one or more parameters of interest are estimated based on spectral measurements of wafers under process using a trained signal response metrology (SRM) measurement model. In another aspect, a trained signal decontamination model is employed to generate decontaminated optical spectra from measured optical spectra while the wafer is being processed.

25 Claims, 10 Drawing Sheets

(51) Int. Cl.
*G01B 11/06* (2006.01)
*G01N 21/95* (2006.01)
*G03F 7/20* (2006.01)
*G01B 11/24* (2006.01)
*G01N 21/21* (2006.01)

(52) U.S. Cl.
CPC ....... *G01N 21/255* (2013.01); *G01N 21/9503* (2013.01); *G03F 7/705* (2013.01); *G03F 7/70625* (2013.01); *H01L 22/26* (2013.01); *G01B 2210/56* (2013.01); *G01N 2021/213* (2013.01)

(58) Field of Classification Search
USPC .................................. 356/630, 369, 301, 326
See application file for complete search history.

(56) References Cited

U.S. PATENT DOCUMENTS

| | | | |
|---|---|---|---|
| 5,859,424 A | 1/1999 | Norton et al. | |
| 5,877,859 A | 3/1999 | Aspnes et al. | |
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,764,379 B2 | 7/2004 | Finarov | |
| 6,816,570 B2 | 10/2004 | Janik et al. | |
| 6,895,075 B2 | 5/2005 | Yokhin et al. | |
| 6,917,433 B2 | 7/2005 | Levy et al. | |
| 6,972,852 B2 | 12/2005 | Opsal et al. | |
| 6,985,618 B2 | 1/2006 | Adel et al. | |
| 7,105,059 B2* | 9/2006 | Lee .................. C23C 16/45544 118/712 | |
| 7,248,375 B2 | 7/2007 | Opsal et al. | |
| 7,352,453 B2 | 4/2008 | Mieher et al. | |
| 7,463,369 B2 | 12/2008 | Wack et al. | |
| 7,478,019 B2 | 1/2009 | Zangooie et al. | |
| 7,502,101 B2 | 3/2009 | Raymond et al. | |
| 7,715,019 B2 | 5/2010 | Kiers et al. | |
| 7,719,677 B2 | 5/2010 | Rosengaus | |
| 7,734,437 B2 | 6/2010 | Tian et al. | |
| 7,826,071 B2 | 11/2010 | Shchegrov et al. | |
| 7,929,667 B1 | 4/2011 | Zhuang et al. | |
| 7,933,026 B2 | 4/2011 | Opsal et al. | |
| 8,030,631 B2 | 10/2011 | Norton et al. | |
| 8,248,617 B2 | 8/2012 | De Groot et al. | |
| 8,441,639 B2 | 5/2013 | Kandel et al. | |
| 8,570,531 B2 | 10/2013 | Li | |
| 8,699,027 B2 | 4/2014 | Wolf et al. | |
| 8,766,215 B2 | 7/2014 | Koya | |
| 9,383,661 B2 | 7/2016 | Pandev | |
| 2003/0153102 A1 | 8/2003 | Chiu et al. | |
| 2004/0032593 A1* | 2/2004 | Venugopal ......... G01B 11/0625 356/504 | |
| 2005/0020073 A1* | 1/2005 | Perry .................. G01N 21/272 438/689 | |
| 2006/0009872 A1 | 1/2006 | Prager et al. | |
| 2011/0043791 A1 | 2/2011 | Smilde et al. | |
| 2011/0229830 A1 | 9/2011 | Bhattacharyya et al. | |
| 2011/0310388 A1 | 12/2011 | Hill et al. | |
| 2012/0120396 A1 | 5/2012 | Kandel et al. | |
| 2013/0042089 A1 | 2/2013 | Vihn et al. | |
| 2013/0114085 A1 | 5/2013 | Wang et al. | |
| 2013/0141730 A1 | 6/2013 | Quintanilha | |
| 2013/0215404 A1 | 8/2013 | Den Boef | |
| 2013/0229661 A1 | 9/2013 | Kandel et al. | |
| 2014/0106477 A1 | 4/2014 | Chen et al. | |
| 2014/0111791 A1 | 4/2014 | Manassen et al. | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |
| 2015/0204664 A1 | 7/2015 | Bringoltz et al. | |
| 2016/0003609 A1 | 1/2016 | Shchegrov et al. | |
| 2016/0109375 A1 | 4/2016 | Pandev et al. | |
| 2016/0161245 A1 | 6/2016 | Fu et al. | |

* cited by examiner

METROLOGY SYSTEMS AND METHODS FOR PROCESS CONTROL

CROSS REFERENCE TO RELATED APPLICATION

The present application for patent claims priority under 35 U.S.C. § 119 from U.S. provisional patent application Ser. No. 62/407,658, entitled "Metrology System and Method for Etch Process Control," filed Oct. 13, 2016, the subject matter of which is incorporated herein by reference in its entirety.

TECHNICAL FIELD

The described embodiments relate to metrology systems and methods, and more particularly to methods and systems for improved measurement of semiconductor structures undergoing a fabrication process step.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. Optical metrology techniques offer the potential for high throughput without the risk of sample destruction. A number of optical metrology based techniques including scatterometry and reflectometry implementations and associated analysis algorithms are commonly used to characterize critical dimensions, film thicknesses, composition, overlay and other parameters of nanoscale structures.

In semiconductor device manufacturing, etch processes and deposition processes are critical steps to define a device pattern profile and layout on a semiconductor wafer. Thus, it is important to measure films and patterned structures to ensure the fidelity of the measured structures and their uniformity across the wafer. Furthermore, it is important to provide measurement results quickly to control the on-going process and to adjust settings to maintain required pattern or film uniformity across the wafer.

In most examples, precise monitoring of a semiconductor manufacturing process is performed by one or more stand-alone (SA) metrology systems. SA metrology systems usually provide the highest measurement performance. However, the wafer must be removed from the process tool for measurement. For processes undertaken in vacuum, this causes significant delay. As a result, SA metrology systems cannot provide fast measurement feedback to process tools, particularly process tools involving vacuum. In other examples, integrated metrology systems or sensors are often attached to process equipment to measure wafers after a process step is completed, but without removing the wafer from the process tool. In other examples, in-situ (IS) metrology systems or sensors are employed inside a processing chamber of a process tool. Furthermore, an IS metrology system monitors the wafer during the process (e.g., etch process, deposition process, etc.) and provides feedback to the process tool performing the fabrication step under measurement.

In one example, structures subject to a reactive ion etch process are monitored in-situ. In some fabrication steps, the etch process is required to etch completely through an exposed layer and then terminate before substantial etching of a lower layer occurs. Typically, these process steps are controlled by monitoring the spectral signature of the plasma present in the chamber using an emission spectroscopy technique. When the exposed layer is etched through and the etch process begins to react with a lower layer, a distinct change in the spectral signature of the plasma occurs. The change in spectral signature is measured by the emission spectroscopy technique, and the etch process is halted based on the measured change is spectral signature.

In other fabrication steps, the etch process is required to etch partially through an exposed layer to a specified etch depth, and terminate before etching completely through the exposed layer. This type of etch process is commonly referred to as a "blind etch". Currently, the measurement of etch depth through partially etched layers is based on near-normal incidence spectral reflectometry.

In some examples, the wafer under measurement includes periodic patterns. These patterns exhibit unique reflectivity signatures that can be modeled. Thus, model based spectral reflectometry measurement techniques are suitable for estimating critical dimensions of patterned wafers. Unfortunately, currently available in-situ monitoring tools based on spectral reflectometry lack the precision required to meet future fabrication process requirements.

In some examples, scatterometry-based IM and IS systems are employed in the semiconductor industry. Exemplary IM and IS systems are described in U.S. Pat. No. 6,917,433 assigned to KLA-Tencor Corporation, the contents of which are incorporated herein by reference. An optical endpoint detection metrology system that compares a measured signal to a pre-determined "endpoint" signal or calibration curve is disclosed in U.S. Pat. No. 6,764,379, assigned to Nova Measuring Instruments, Inc., the contents of which are incorporated herein by reference. Although the aforementioned patent documents describe tools and methods for controlling etch and deposition processes, they are unable to determine process endpoints for complex patterns fabricated on modern semiconductor wafers with multiple pattern layouts under measurement. For example, current IS or IM systems fail to account for multiple process parameters that affect the measured signal. Although etch or deposition time is one process parameter impacting the measured device structure, there are other process parameters that affect the measured structure in a similar manner. The inability of prior art systems to account for multiple parameters affecting the measured signal limits their measurement effectiveness, particularly for complex patterned structures.

In many practical examples, the semiconductor wafer under measurement includes homogeneous regions of periodic patterns and also non-homogeneous regions including support circuitry, scribe lines, etc. For example, on a memory wafer, the typical size of the homogeneous region is about 50 microns square surrounded by a non-homogeneous region of a few microns surrounding the homogeneous region. Currently available in-situ monitoring tools illuminate the wafer with a collimated beam that illuminates a large circular area of the wafer, including homogeneous and non-homogeneous regions. Typical illumination spot sizes are ten millimeters in diameter, or larger. The reflected light collected over this large area is mixed and analyzed by a spectrometer. Mixing the reflectivity signals from homogeneous and non-homogeneous regions on the wafer fundamentally limits the performance of the metrology system (i.e., measurement accuracy is limited).

The problem of mixing of reflectivity signals from homogeneous and non-homogeneous regions of the wafer is difficult to solve optically because it is not possible to place illumination and collection optics near the wafer within the reactive plasma chamber. This limits the maximum achievable numerical aperture (NA) and the minimum achievable illumination spot size. Without the ability to optically focus on a small homogeneous region of the wafer with minimum spill-over onto the surrounding non-homogeneous region, current systems cannot overcome the limits to measurement accuracy due to mixing of reflected signals.

In summary, ongoing reductions in feature size impose difficult requirements on IM and IS metrology systems, particularly those integrated with etch and ion implant process tools. Optical metrology systems must meet high precision and accuracy requirements to enable adequate process control. Thus, improved metrology systems and methods are desired to measure films and patterned structures to ensure their fidelity and uniformity across the wafer.

SUMMARY

Methods and systems for estimating values of process parameters, structural parameters, or both, based on repeated measurements of a wafer during a process interval are presented herein. In one aspect, one or more optical metrology subsystems are integrated with a process tool, such as an etch tool or a deposition tool. Values of one or more parameters of interest measured while the wafer is being processed are used to control the process itself. The measurements are performed quickly and with sufficient accuracy to enable yield improvement of a semiconductor fabrication process flow.

In one aspect, values of one or more parameters of interest are estimated based on spectral measurements of wafers under process using a trained signal response metrology (SRM) measurement model.

In a further aspect, a SRM measurement model is trained based on Design of Experiments (DOE) spectra. The DOE spectra are either measured from one or more DOE wafers by the metrology subsystem of the process tool or simulated. DOE wafers, or simulated DOE, include variations of critical and non-critical structural parameters, etch process conditions and settings, wafers fabricated in different etch chambers, etc. DOE values of parameters of interest associated with the DOE spectra are estimated by direct measurement by a reference metrology tool, simulation, or a combination thereof. The DOE spectra and the DOE values of the parameters of interest are employed to train the SRM measurement model. The trained SRM measurement model provides a transfer function from measured spectral signals to values of parameters of interest.

In general, spectral signals are generated by measurements of a wafer undergoing a process that changes the physical characteristics of the structure(s) under measurement over time. In some examples, spectral signals include spectral signals collected by the metrology subsystem at a single point in time. However, in a further aspect, each instance of a spectral measurement includes spectral signals collected by the metrology subsystem at the current time and at one or more previous times within a process interval.

In another further aspect, reference measurements are performed at a limited number of times within a process interval and reference measurement values associated with any instance within the process interval is determined by interpolation.

In another further aspect, values of parameters of interest and corresponding spectra employed to train the SRM measurement model are derived synthetically by simulation of the optical response of the metrology subsystem for a set of DOE shape profiles. The DOE shape profiles are generated synthetically based on the different values of the one or more parameters of interest (e.g., etch depth), along with static or varying values of other shape parameters necessary to describe the DOE profile.

In another further aspect, synthetically generated values of parameters of interest and corresponding spectra employed to train a SRM measurement model are constrained based on correlations among shape parameters derived from measured data.

In another further aspect, synthetically generated values of parameters of interest and corresponding spectra employed to train a SRM measurement model are constrained based on simulations of expected shape profiles by a process simulator (e.g., etch process simulator).

In another further aspect, a SRM measurement model trained based on synthetic measurement data is further optimized based on actual measured spectra and corresponding reference measurement data. In some examples, a trained SRM measurement model is further optimized (e.g., measurement model parameters are tuned) to minimize precision errors, repeatability errors, DOE tracking errors, chamber to chamber mismatch, etc.

In another aspect, a trained signal decontamination model is employed to generate decontaminated optical spectra from measured optical spectra while the wafer is being processed. The decontaminated spectra are employed to determine values of parameters of interest by physical model based regression, library regression, or an SRM measurement model as described herein. The parameters of interest are provided as feedback to control the process tool.

A signal decontamination model is trained based on optical spectra collected from one or more DOE wafers measured by a metrology subsystem of a process tool. DOE wafers include variations of critical and non-critical structural parameters, etch process conditions and settings, wafers fabricated in different etch chambers, etc. Values of parameters of interest associated with the DOE wafers are estimated by measurement by a reference metrology tool. Furthermore, decontaminated spectra are simulated based on the measured values of the parameters of interest. The measured spectra and the decontaminated spectra are employed to train the signal decontamination model. The trained signal decontamination model provides a transfer function from measured spectral signals to decontaminated spectra useable to estimate values of one or more parameters of interest. In general, the trained decontamination model isolates spectral variations induced by variations of one or more parameters of interest from spectral variations induced by variations of other parameters or sources of measurement noise.

In another aspect, one or more metrology systems integrated with a process tool are configured to measure multiple, different areas of a wafer during a process interval. Estimated values of one or more parameters of interest are determined using a trained SRM measurement model, a trained signal decontamination model, or both, as described herein. In some embodiments, a wafer uniformity value associated with each measured parameter of interest is determined based on measured values of each parameter of interest across the wafer. In some embodiments, a wafer uniformity value associated with each measured parameter of interest is determined based on measured spectra at multiple, different areas across the wafer. In these embodiments, a trained SRM measurement model determines the wafer uniformity value associated with each measured parameter of interest based on the measured spectra at multiple, different areas across the wafer.

In some embodiments, multiple metrology systems are integrated with the process tool and the metrology systems are configured to simultaneously measure different areas across the wafer during process. In some embodiments, a single metrology system integrated with a process tool is configured to sequentially measure multiple, different areas of a wafer during process.

In some embodiments, different areas of the wafer under process include metrology targets having different structures. In these embodiments, a SRM measurement model, a signal decontamination model, or both, are configured as multiple target models (i.e., training and measurement during process are performed on multi-target spectra).

In a further aspect, the determination of values of one of more parameters of interest at a particular time during a process interval involves values of one or more parameters determined by external reference metrology or in-situ metrology at a previous step of the process.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for estimating values of process parameters, structural parameters, or both, based on repeated measurements of structures undergoing a wafer fabrication process step are presented herein. Measurements performed while the wafer is being processed are used to control the on-going process. Exemplary processes include etch and deposition processes. The measurements are performed quickly and with sufficient accuracy to enable yield improvement of an on-going semiconductor fabrication process flow.

In one aspect, an optical metrology system is integrated with a process tool. A trained signal response metrology (SRM) measurement model is employed to determine values of parameters of interest (e.g., etch depth) directly from measured optical spectra while the wafer is being processed. The values of the parameters of interest are provided as feedback to control the process tool.

In another aspect, a SRM measurement model is trained based on Design of Experiments (DOE) spectra. The DOE spectra are either measured from one or more DOE wafers by the metrology subsystem of the process tool or simulated. DOE wafers, or simulated DOE, include variations of critical and non-critical structural parameters, etch process conditions and settings, wafers fabricated in different etch chambers, etc. DOE values of parameters of interest associated with the DOE spectra are estimated by direct measurement by a reference metrology tool, simulation, or a combination thereof. The DOE spectra and the DOE values of the parameters of interest are employed to train the SRM measurement model. The trained SRM measurement model provides a transfer function from measured spectral signals to values of parameters of interest.

Figure 1:
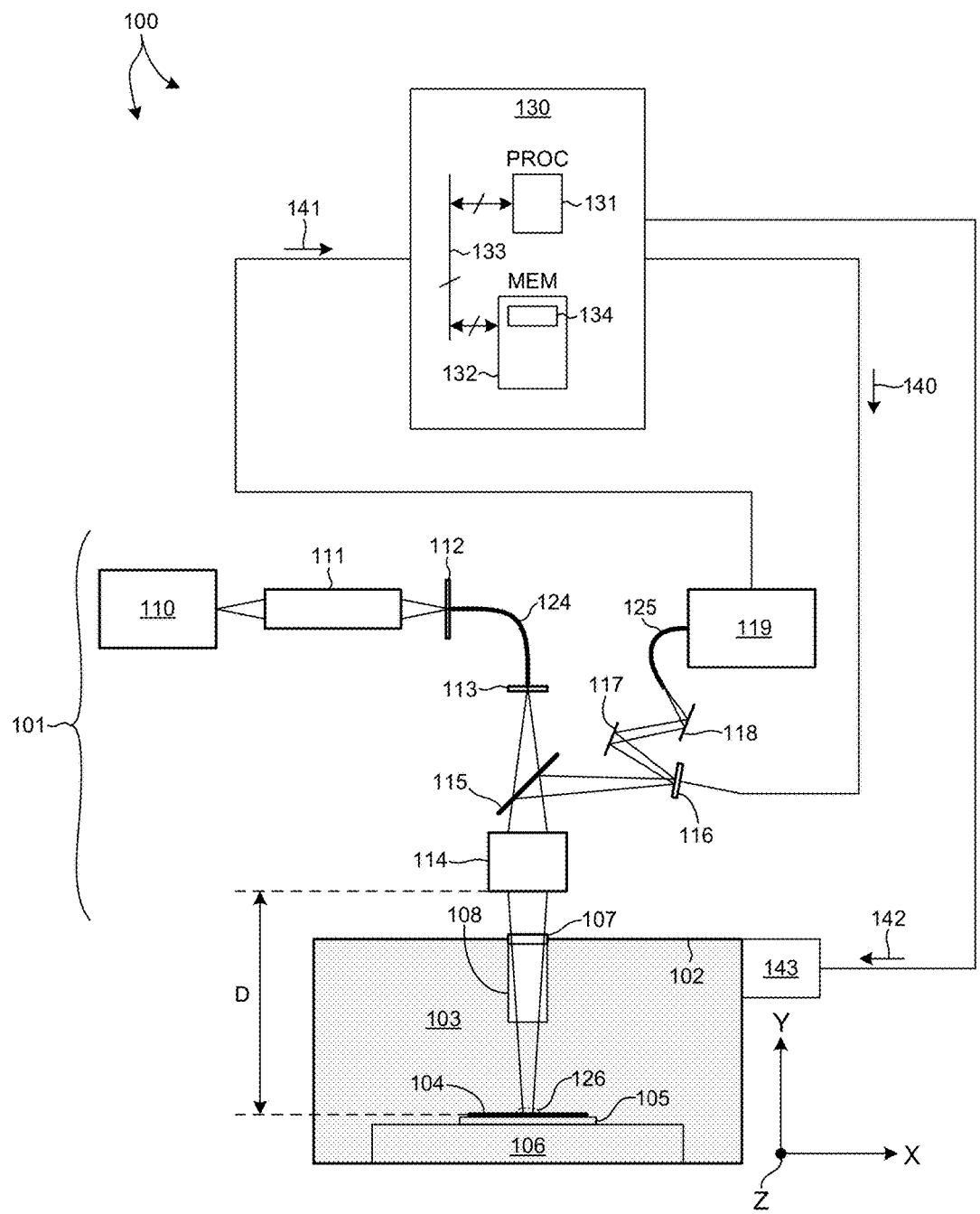
FIG. 1 depicts an illustration of a wafer processing system 100 including a metrology subsystem 101 for monitoring characteristics of a wafer in accordance with the exemplary methods presented herein while the wafer is under process.

FIG. 1 depicts an exemplary wafer processing system 100 for monitoring of an etch process based on spectral reflectometry measurements of semiconductor structures disposed on a wafer under process.

Wafer processing system 100 includes a process chamber 102 containing a process environment 103 and a selective spectral reflectometer (SSR) 101. Semiconductor wafer 104 is located within process chamber 102. Wafer 104 is attached to wafer chuck 105 and is positioned with respect to process chamber 102 by wafer stage 106. In some embodiments, wafer stage 106 combines a rotational movement with a translational movement (e.g., a translational movement in the X direction and a rotational movement about the Y-axis) to position wafer 104 with respect to the illumination provided by SSR 101. In some other embodiments, wafer stage 106 combines two orthogonal, translational movements (e.g., movements in the X and Z directions) to position wafer 104 with respect to the illumination provided by SSR 101. In some embodiments, wafer processing system 100 does not include wafer stage 106. In these embodiments, a wafer handling robot (not shown) locates wafer 104 on wafer chuck 105 inside process chamber 102. Wafer 104 is transferred from the wafer handling robot onto an electrostatic wafer chuck 105 that is compatible with a vacuum process environment 103. In these embodiments, the measurements performed by SSR 101 are limited to the portion of wafer 104 within the field of view of SSR 101 after clamping of wafer 104 onto wafer chuck 105. In this sense, wafer stage 106 is optional. To overcome this limitation, wafer processing system 100 may include multiple SSR systems, each measuring a different area of wafer 104.

In one embodiment, process chamber 102 is an element of a reactive ion etch system. In this embodiment, process environment 103 includes a radio frequency induced plasma that etches away exposed material on the surface of wafer 104.

As depicted in FIG. 1, the optical elements of SSR 101 are located outside of the process chamber 102. In some embodiments, all of the optical elements of SSR 101 are located at least a distance, D, from wafer 104. In some of these embodiments, D is at least 300 millimeters. In some other embodiments, D is at least 600 millimeters. Ionized particles are present in the process chamber of both etch and depositions processes. Optical elements must be located sufficiently far away from the wafer to avoid disturbing the magnetic fields induced by the process. In addition, ionized particles may accumulate on optical elements located in the process chamber, and thus it is not practical to include the optical elements in the process chamber.

SSR 101 includes an illumination source 110 that generates a beam of illumination light incident on a measurement spot on the surface of wafer 104. Illumination source 110 is a broadband illumination source. In some embodiments, illumination source 110 emits illumination light in the ultraviolet, visible, and infrared spectra. In one embodiment, illumination source 110 is a laser driven light source (LDLS) (a.k.a., laser driven plasma source or laser sustained plasma light source). The pump laser of the LDLS 110 may be continuous wave or pulsed. A LDLS can produce significantly more photons than a Xenon lamp across the entire wavelength range from 150 nanometers to 2000 nanometers. In general, illumination source 110 can be a single light source or a combination of a plurality of broadband or discrete wavelength light sources. The light generated by illumination source 110 includes a continuous spectrum or parts of a continuous spectrum, from ultraviolet to infrared (e.g., vacuum ultraviolet to mid infrared). In general, illumination light source 110 may include a super continuum laser source, an infrared helium-neon laser source, an arc lamp, or any other suitable light source.

In a further aspect, the broadband illumination light provided to wafer 104 is broadband illumination light that includes a range of wavelengths spanning at least 500 nanometers. In one example, the broadband illumination light includes wavelengths below 250 nanometers and wavelengths above 750 nanometers. In general, the broadband illumination light includes wavelengths between 120 nanometers and 3,000 nanometers. In some embodiments, broadband illumination light including wavelengths beyond 3,000 nanometers may be employed.

As depicted in FIG. 1, SSR 101 includes optical elements configured to direct illumination light to, and collect reflected light from, wafer 104. The optical subsystem is shown to include a light pipe 111, a chopper 112, an optical fiber 124, an illumination field stop 113, focusing optics 114, beam splitter 115, relay optics 117 and 118, and optical fiber 125. In some embodiments, SSR 101 includes one or more optical filters (not shown) used to control light level, spectral output, or both, from the illumination source.

As depicted in FIG. 1, light emitted from illumination source 110 is coupled to light pipe 111. In some embodiments, light pipe 111 is a tapered light pipe that effectively functions as an illumination field stop to match the NA of the illumination optics. Light from light pipe 111 passes through chopper 112. Light from a continuous source is chopped by chopper 112 located at or near the focal point at the entrance of illumination fiber 124. In some embodiments, chopper 112 is a resonant piezoelectric driven tuning fork. A resonant tuning fork device is electrically driven and the oscillatory frequency of the tuning force device is easily adjusted to match with process frequencies (e.g., plasma frequency) to ensure that measurements are performed when the process is active. In some other embodiments, a rotary chopper mechanism is employed. In these embodiments, the rotational velocity of the chopper mechanism is adjusted to match with process frequencies.

Chopper 112 is synchronized with the data collection of SSR 101 to alternately allow and block illumination light from reaching wafer 104. During a period of time when the illumination light is blocked by chopper 112, background images (e.g., "dark" images) are collected by SSR 101. When the illumination light is not blocked by chopper 112, images of wafer 104 (e.g., "bright" images) are collected by SSR 101.

In a further aspect, a computing system (e.g., computing system 130 or a computing system of spectrometer 119) is configured to subtract background images from "bright" images to remove the effects of stray light collected from sources other than illumination source 110 from the spectral results obtained by spectrometer 119. In one example, plasma emission collected along the optical path is a significant source of background noise present in a "bright" image, and effectively isolated in a "dark" image. In one example, the computing system determines a difference between an amount of collected light at the spectrometer when the optical path is not blocked by the chopper and an amount of collected light at the spectrometer when the optical path is blocked by the chopper. This difference is spectrally analyzed to generate the output signal 141 communicated to computing system 130. In another example, computing system 130 receives spectral signals associated with both "dark" and "bright" images, and determines a spectral difference between the two signals.

In some other embodiments, illumination source 110 is a pulsed light source. In some of these embodiments, the frequency of the pulsed light source is tuned to match process frequencies. In these embodiments, it is not necessary to employ a chopper. In this sense, chopper 112 is optional.

As depicted in FIG. 1, illumination light passes through illumination fiber 124 and through illumination field stop 113 located at or near the focal point at the exit of illumination fiber 124. The illumination source 110 is imaged into illumination fiber 124 to allow for design freedom in the physical layout of the optical system. In some other embodiments, the illumination source is directly coupled to focusing optics 114. Illumination field stop 113 controls the field of view (FOV) of the illumination subsystem and may include any suitable commercially available field stop. Light from illumination source 110 is focused by focusing optics 114 on one or more structures disposed on wafer 104 (e.g., a die) over a measurement spot 126 representative of the field of view of the SSR system. In some embodiments, the measurement spot 126 is circular in shape and approximately three millimeters in diameter. In some embodiments, the measurement spot 126 is circular in shape and less than four millimeters in diameter. In general, the measurement spot 126 may be shaped in any suitable manner.

Illumination and collected light passes one or more window elements 107 gas injector system 108 of process chamber 102. In some embodiments, window element 107 is fabricated from sapphire. However, in general, any suitable optical material may be employed. Gas injector system 108 extends from window element 107 into process chamber 102. In one embodiment, the distance from window element 107 and wafer 104 is approximately 300 millimeters and gas injector system 108 extends approximately 150 millimeters from window elements 107 toward wafer 104. Gas injector system 108 introduces a gas flow along the optical path to prevent ionized gas particles from impacting and contaminating window elements 107. Exemplary gas injector systems are manufactured by LAM Research Corporation, Fremont, Calif. (USA).

Light is reflected from wafer 104 in response to the illumination provided by illumination source 110. The optical subsystem collects the reflected light from the measurement spot 126. Reflected light passes through window elements 107, focusing optics 114, and is directed toward DMA 116 by beam splitting element 115.

As depicted in FIG. 1, SSR 101 includes a DMA 116. The wafer surface under measurement is imaged to an active surface of the DMA and light reflected from selected DMA pixels is coupled into a large core fiber connected to a fiber coupled spectrometer for capture of spectroscopic information. Specific regions of the image incident on DMA 116 are selected to improve measurement accuracy by discarding portions of the reflected light associated with regions that are inaccurately modelled, or otherwise distort the measurement of one or more parameters of interest.

In some embodiments DMA 116 is a DLP® chip manufactured by Texas Instruments, Inc., Dallas, Tex. (USA). The DLP® chip includes an array of mirror elements selectably positioned in one of two positions. In one position, light is reflected (i.e., directed toward the light source), and in the other position, light is effectively blocked or otherwise removed from the optical path of SSR 101 (i.e., reflected away from the light source). Other DMA implementations may be contemplated, e.g., implementations based on other DMA architectures such as those developed by the Fraunhofer Institute (Germany).

As depicted in FIG. 1, command signals 140 indicative of a desired state of each of the mirror elements of DMA 116 are communicated from computing system 130 to DMA 116. In response, DMA 116 adjusts one or more of the array of mirror elements to achieve the desired state of DMA 116. In some embodiments, the pitch of the array of mirror elements is approximately 10 micrometers. With an optical system designed for 1:1 imaging, DMA 116 has sufficient resolution to select small sized regions on the wafer dominated by patterns to be controlled having small sizes (e.g., regions of interest sized 50 micrometers by 50 micrometers, or even smaller).

In the embodiment depicted in FIG. 1, the selected amount of collected light is directed to collection fiber 125 by relay optics 117 and 118. Collection fiber 125 is coupled to spectrometer 119. Spectrometer 119 generates an output signal 141 responsive to the selected amount of light collected from one or more structures illuminated by the illumination source. In the depicted example, output signal 141 is indicative of a spectral response of the selected amount of light.

In some embodiments (not shown), the optical subsystem includes a collection field stop to control the FOV of the collection subsystem. In some embodiments, a collection field stop is used as a spectrometer slit for the spectrometer 119. However, a collection field stop may be located at or near a spectrometer slit of the spectrometer 119.

In general, the optical subsystem may include any type and arrangement of optical filter(s), field stops, aperture stops, fibers, etc. known in the art of spectroscopic reflectometry. For example, fibers 124 and 125 are optional as light may be directly coupled to spectrometer 119 and focusing optics 114. The use of optical fibers may be advantageous in the design of in-situ SSR systems where space is highly constrained by other process tool hardware.

In one aspect, computing system 130 is configured as a process control metrology model training engine to train a SRM measurement model employed to directly estimate process parameter values based on measurements of structures under measurement.

In a further aspect, values of parameters of interest employed to train the SRM measurement model are derived from measurements of DOE wafers by a reference metrology system. The reference metrology system is a trusted measurement system that generates sufficiently accurate measurement results, albeit slowly. Such reference metrology systems are too slow to be used to measure wafers on-line as part of the wafer fabrication process flow, but are suitable for off-line use for purposes such as model training. By way of non-limiting example, a reference metrology system may include a stand-alone optical metrology system, such as a spectroscopic ellipsometer (SE), SE with multiple angles of illumination, SE measuring Mueller matrix elements, a single-wavelength ellipsometer, a beam profile ellipsometer, a beam profile reflectometer, a broadband reflective spectrometer, a single-wavelength reflectometer, an angle-resolved reflectometer, an imaging system, a scatterometer, such as a speckle analyzer, an X-ray based metrology system such as a small angle x-ray scatterometer (SAXS) operated in a transmission or grazing incidence mode, an x-ray diffraction (XRD) system, an x-ray fluorescence (XRF) system, an x-ray photoelectron spectroscopy (XPS) system, an x-ray reflectometer (XRR) system, a Raman spectroscopy system, an atomic force microscopy (AFM) system, a transmission electron microscopy system, a scanning electron microscopy system, or other technologies capable of determining device geometry but not optimized for integrated or in-situ operation.

Figure 2:
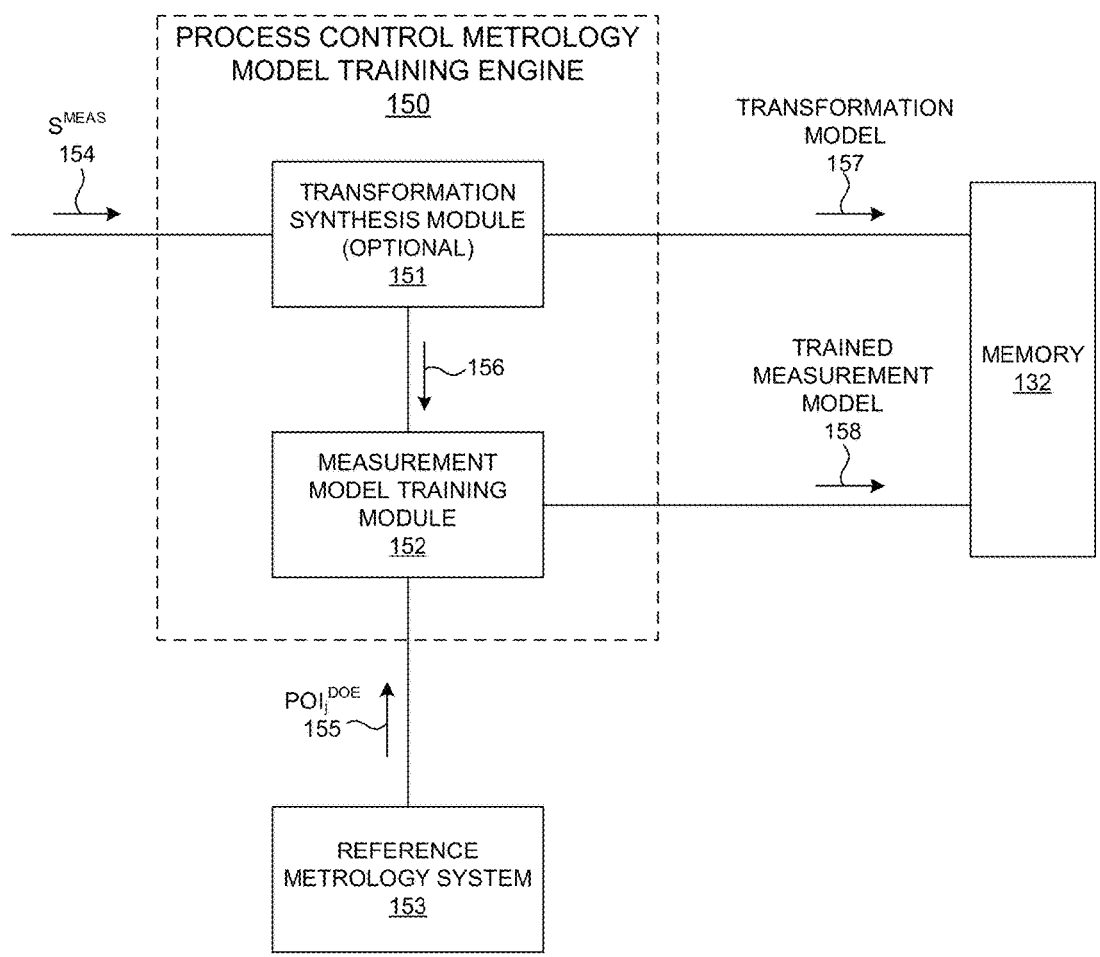
FIG. 2 is a diagram illustrative of an exemplary process control metrology model training engine 150 in one embodiment.

FIG. 2 is a diagram illustrative of an exemplary process control metrology model training engine 150 in one embodiment. As depicted in FIG. 2, process control metrology model training engine 150 includes a transformation synthesis module 151 and a measurement model training module 152.

As depicted in FIG. 2, transformation synthesis module 151 determines a transformation model 157 and applies the transformation model to measured spectral signals 154 to generate a reduced set of signals 156. In one example, measured spectral signals 154 are associated with measurements of a DOE wafer set measured by metrology system 101. In this example, measured spectral signals 154 correspond with signals 141 depicted in FIG. 1. In general, spectral signals 154 are associated with measurements of a DOE wafer set by any metrology system integrated with a fabrication process tool. In general, the DOE wafer set includes variations over critical and non-critical parameters, etch process conditions and settings, wafers from different etch chambers, etc. Furthermore, the same wafers are characterized by reference metrology tool 153 to generate estimated values of parameters of interest, $POI_j^{DOE}$ 155.

Transformation synthesis module 151 determines a transformation model 157 that reduces a dimension of the measured spectral data, $S^{MEAS}$ 154. The transformation model 157 maps signals 154 to a new reduced set of signals 156. The transformation is determined based on the variations in the parameter(s) of interest in the set of signals 154. Each signal is treated as an original signal that changes within the process range. The transformation model 157 may be applied to all signals 154, or a subset of signals 154. In some examples, the signals subject to analysis by the transformation model are chosen randomly. In some other examples, the signals subject to analysis by the transformation model are chosen due to their relatively high sensitivity to changes in the process parameter(s) of interest. For example, signals that are not sensitive to changes in the process parameter(s) of interest may be ignored. In some examples, a transformation model is not employed at all. In this sense, transformation synthesis module 151 is optional.

In general, any of the transformation models described herein may be linear or non-linear. By way of non-limiting example, a transformation model may be a principal component analysis (PCA) model, a kernel PCA model, a non-linear PCA model, an independent component analysis (ICA) model, a trained auto-encoder, or other dimensionality reduction methods using dictionaries, a discrete cosine transform (DCT) model, fast fourier transform (FFT) model, a wavelet model, etc. In addition, any of the transformation models described herein may include interpolation, noise reduction, etc. As described herein, the use of transformation models described herein is optional.

As depicted in FIG. 2, the reduced set of signals 156 is received by measurement model training module 152. Measurement model training module 152 trains a measurement model 158 that establishes a functional relationship between measurements of actual structures and values of parameters of interest, including one or more process parameter values associated with the fabrication process of system 100. Measurement model training module 152 receives the DOE set of values of one or more parameters of interest, $POI_j^{DOE}$ 155 from reference metrology system 153, and corresponding reduced measurement signals 156 associated with each point in the DOE space. The received data is used to train the measurement model that predicts values of parameters of interest from actual, reduced measurement signals.

In general, any of the trained models described herein is a signal response metrology (SRM) model. In some examples, measurement model 158 is a signal response metrology (SRM) model that defines a direct, functional relationship between actual measurements and parameters of interest.

In general, any of the trained models described herein is implemented as a neural network model. In other examples, any of the trained models may be implemented as a linear model, a non-linear model, a polynomial model, a response surface model, a support vector machines model, a decision tree model, a random forest model, a deep network model, a convolutional network model, or other types of models.

In some examples, any of the trained models described herein may be implemented as a combination of models.

Transformation model 157 and trained measurement model 158 are communicated from process control metrology model training engine 150 to a memory (e.g., memory 132), where they are stored.

In general, spectral signals 154 are generated by measurements of a wafer undergoing a process that changes the physical characteristics of the structure(s) under measurement over time. In some examples, spectral signals 154 may include spectral signals collected by metrology system 101 at a single point in time. However, in a further aspect, each instance of spectral signals 154 includes spectral signals collected by metrology system 101 over several points in time. In some examples, each instance of spectral signals 154 includes signals collected at the current time and at previous times within the process interval as illustrated by Equation (1), where $S_t^{MEAS}$ is a vector of measured spectral signals at instance, t, $S_t$ are spectral signals associated with the measurement at time, t, $S_{t-1}$ are spectral signals associated with the measurement immediately prior to time, t, $S_{t-2}$ are spectral signals associated with the measurement immediately prior to time, t−1, etc.

$$S_t^{MEAS}=[S_t,S_{t-1},S_{t-2},\ldots,S_{t-k}] \quad (1)$$

For example, a process tool 100 may etch a wafer during a process interval over a period of time (e.g., 80 seconds) and metrology system 101 may collect spectral signals 141 at a particular measurement interval (e.g., every 10 milliseconds) over the duration of the process interval. In one example, each instance of spectral signals 154 may include the collected signals associated with a single measurement. However, in some other examples, each instance of spectral signals 154 may include the collected signals associated with a time-series of measurements (e.g., collected signals associated with the current measurement interval and a number of previous intervals). In these examples, each instance of spectral signals 154 is a vector of spectral signals including spectral signals associated with the current measurement interval and the previous number of measurement intervals. In some examples, the number of measurement intervals included in an instance of spectral signals 154 is 10 or less.

It may be advantageous to train an SRM measurement model and use the trained SRM measurement model with spectral signals associated with a series of measurement times, rather than a single point in time. Using spectral signals associated with a series of measurement times may break correlations among parameters of interest and improve measurement precision by including data associated with a longer optical exposure (i.e., more photons).

Similarly, corresponding values of the DOE set of one or more parameters of interest, $POI_j^{DOE}$ 155, are generated by reference measurements of a wafer undergoing the process that changes the physical characteristics of the structure(s) under measurement over time. If each instance of spectral signals 154 is associated with a single point in time, reference measurements 155 include corresponding measurements at the same, or similar, single point in time within the process duration. However, if each instance of spectral signals 154 is associated with a series of measurement times, reference measurements 155 include corresponding measurements at the same, or similar, series of measurement times within the process duration.

Since the reference metrology system is not integrated with the process tool (e.g., process tool 100), the processing of the wafer must be stopped at a desired point in time within the process duration, removed from the process tool 100, and measured by the reference metrology system 153. This may lead to an excessive amount time if a large number of reference measurements are desired during the process duration.

In a further aspect, reference measurements are performed at a limited number of times within a process interval and reference measurement values 155 associated with any instance within the process interval is determined by interpolation. In one example, a DOE wafer is measured by reference metrology system 153 before wafer processing begins and after wafer processing ends. In this example, reference measurements 155 are directly known at the beginning and end of the process duration. Computing system 130 is further configured to interpolate between these two sets of measurements to estimate the values of the DOE set of one or more parameters of interest, $POI_j^{DOE}$ 155, corresponding with each spectral measurement interval. Equation (2) illustrates an exemplary etch rate function employed to interpolate between reference measurements, where ${}^tPOI_j^{DOE}$ is the value of the jth parameter of interest at time t, and $E_t$ is the etch rate function.

$${}^tPOI_j^{DOE} = E(t) \tag{2}$$

In another further aspect, values of parameters of interest and corresponding spectra employed to train the SRM measurement model are derived synthetically by simulation of the optical response of the integrated metrology system for a set of DOE shape profiles corresponding to each different value of the one or more parameters of interest (e.g., etch depth). The DOE shape profiles are generated synthetically based on the different values of the one or more parameters of interest, along with static or varying values of other shape parameters necessary to describe the DOE profile.

Figure 3:
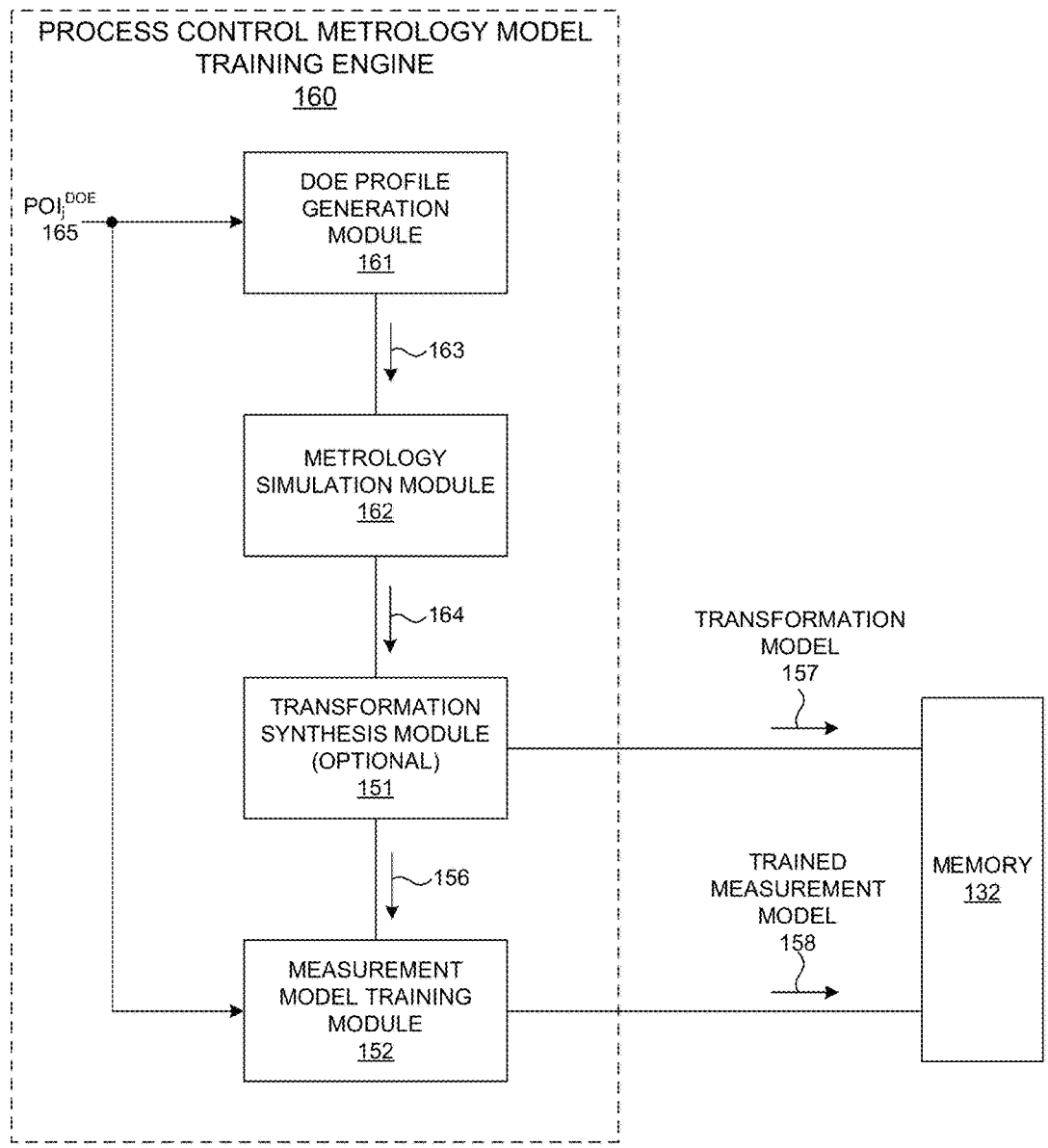
FIG. 3 is a diagram illustrative of an exemplary process control metrology model training engine 160 in another embodiment.

FIG. 3 is a diagram illustrative of an exemplary process control metrology model training engine 160 in one embodiment. As depicted in FIG. 3, process control metrology model training engine 160 includes a transformation synthesis module 151 and a measurement model training module 152 as described with reference to FIG. 2. In addition, process control metrology model training engine 160 includes DOE profile generation module 161 and metrology simulation module 162.

DOE profile generation module 161 generates a set of DOE shape profiles 163 corresponding to each different value of the one or more parameters of interest, $POI_j^{DOE}$ 165. In some embodiments, DOE profile generation module 161 generates DOE shape profiles for each different value of the one or more parameters of interest at a number of different values of other parameters necessary to describe the DOE profile (e.g., sidewall angle, CD, etc.). The range of parameter values is based on the expected range of values of these parameters during actual tool operation. In some examples, the values are chosen programmatically. In other examples, the values are chosen randomly within the desired ranges.

Metrology simulation module 162 generates a set of spectral signals 164 associated with a measurement of each corresponding DOE shape profile 163 by metrology system 101. In some embodiments, the spectral signals 164 are reduced by transformation model 157 in the manner described with reference to FIG. 2. In other examples, spectral signals 164 are employed directly for measurement model training.

As depicted in FIG. 3, measurement model training module 152 generates a trained measurement model 158 based on reduced spectral signals 156 and corresponding values of the one or more parameters of interest 165 in the manner described with reference to FIG. 2. Transformation model 157 and trained measurement model 158 are communicated from process control metrology model training engine 160 to a memory (e.g., memory 132), where they are stored.

In another further aspect, synthetically generated values of parameters of interest and corresponding spectra employed to train a SRM measurement model are constrained based on correlations among shape parameters derived from measured data.

As described with reference to FIG. 3, DOE shape profiles generated by DOE profile generation module 161 and corresponding synthetic spectra generated by metrology simulation module 162 depend on one or more process dependent parameters and process independent parameters. If a range of values of a large number of parameters is simulated, the set of DOE shape profiles and corresponding synthetic spectra may become unreasonably large.

Figure 4:
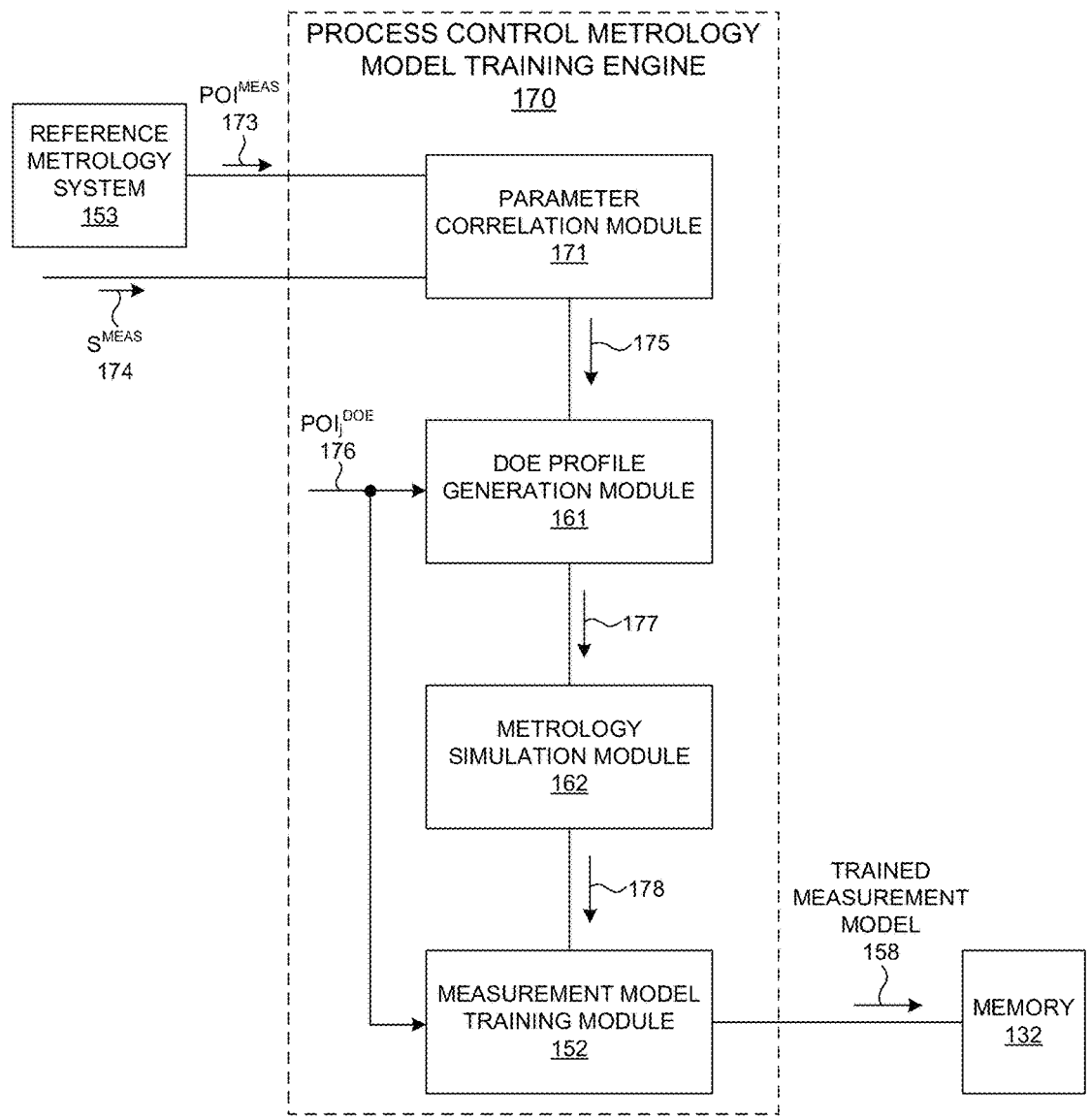
FIG. 4 is a diagram illustrative of an exemplary process control metrology model training engine 170 in another embodiment.

FIG. 4 is a diagram illustrative of an exemplary process control metrology model training engine 170 in one embodiment. As depicted in FIG. 4, process control metrology model training engine 170 includes a DOE profile generation module 161, a metrology simulation module 162 and a DOE measurement model training module 152 as described with reference to FIGS. 2 and 3. In addition, process control metrology model training engine 170 includes parameter correlation module 171.

Parameter correlation module 171 generates a correlation function 175 based on spectral measurements of one or more wafers by metrology system 101 and corresponding values of one or more parameters of interest, $POI^{MEAS}$ 173, measured by reference metrology system 153. The correlation function 175 relates etch dependent parameters and measured profiles. For example, as etch depth changes, so does critical dimension (CD), layer thickness (T), sidewall angle (SWA), etc. Correlation function 175 captures this dependence and effectively reduces the parameter space explored by DOE profile generation module 161. In some examples, correlation function 175 is a covariance matrix relating etch dependent parameters and measured profiles.

DOE profile generation module 161 receives correlation function 175 and generates a set of DOE shape profiles 177 associated with each value of one or more parameters of interest $POI_j^{DOE}$ 176. The set of DOE shape profiles 177 is significantly smaller than the set of DOE shape profiles 163 described with reference to FIG. 3 due to the constraining effect of correlation function 175 on the parameter space explored by DOE profile generation module 161.

Metrology simulation module 162 generates a set of spectral signals 178 associated with a simulated measurement of each corresponding DOE shape profile 177 by metrology system 101. In some embodiments, the spectral signals 178 are reduced by a transformation model in the manner described with reference to FIG. 2. In the example depicted in FIG. 3, spectral signals 178 are employed directly for measurement model training.

As depicted in FIG. 4, measurement model training module 152 generates a trained measurement model 158 based on reduced spectral signals 178 and corresponding values of the one or more parameters of interest 176 in the manner described with reference to FIG. 2. Trained measurement model 158 is communicated from process control metrology model training engine 170 to a memory (e.g., memory 132), where it is stored.

In another further aspect, synthetically generated values of parameters of interest and corresponding spectra employed to train a SRM measurement model are constrained based on simulations of expected shape profiles by a process simulator (e.g., etch process simulator).

As described with reference to FIG. 3, DOE shape profiles generated by DOE profile generation module 161 and corresponding synthetic spectra generated by metrology simulation module 162 depend on one or more process dependent parameters and process independent parameters. If a range of values of a large number of parameters is simulated, the set of DOE shape profiles and corresponding synthetic spectra may become unreasonably large.

Figure 5:
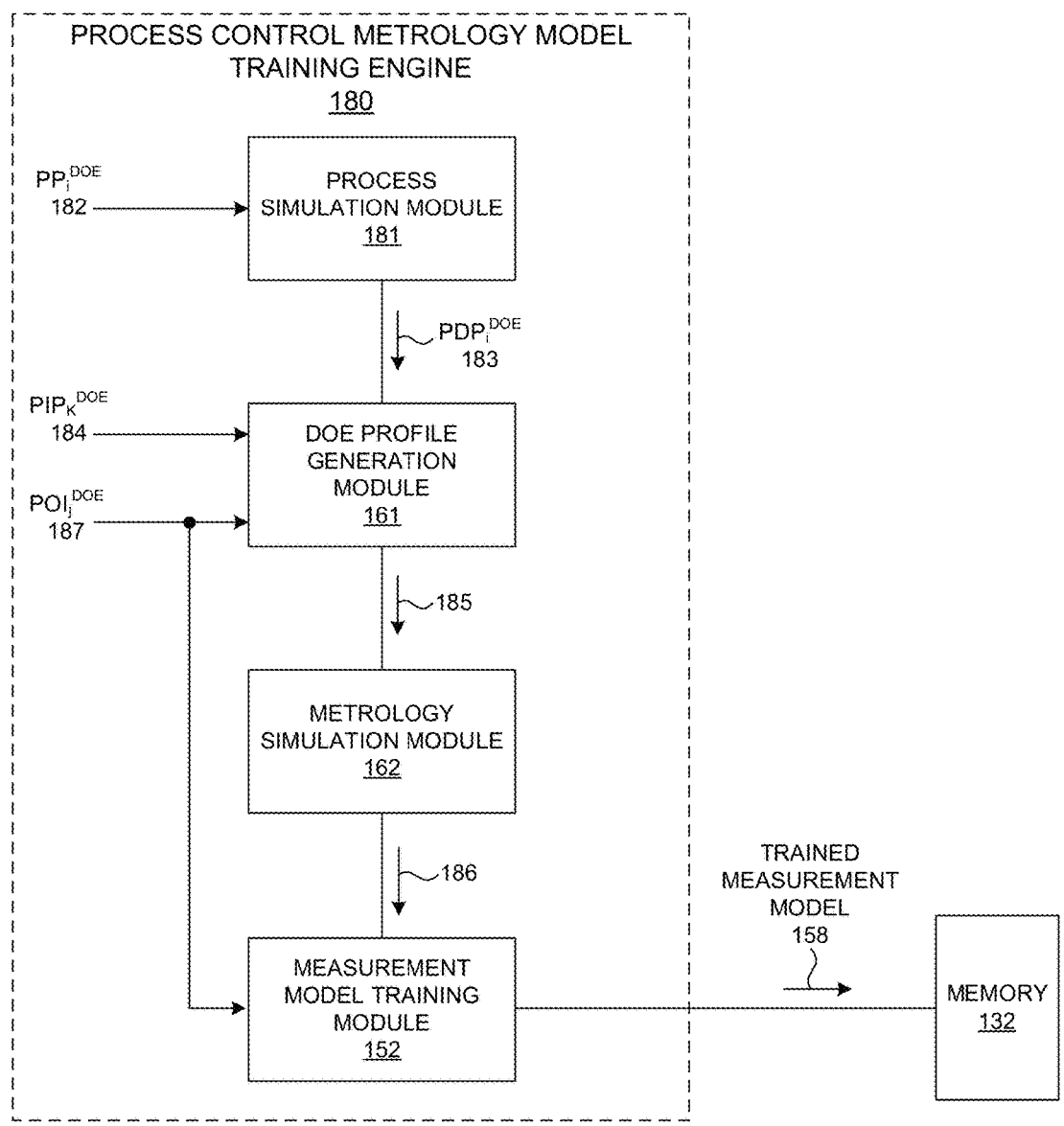
FIG. 5 is a diagram illustrative of an exemplary process control metrology model training engine 180 in another embodiment.

FIG. 5 is a diagram illustrative of an exemplary process control metrology model training engine 180 in one embodiment. As depicted in FIG. 5, process control metrology model training engine 180 includes a DOE profile generation module 161, a metrology simulation module 162 and a DOE measurement model training module 152 as described with reference to FIGS. 2 and 3. In addition, process control metrology model training engine 180 includes process simulation module 181.

Process simulation module 181 generates a set of values for one or more process dependent geometric parameter values, $PDP_j^{DOE}$ 183, based on time varying values of process parameters, $PP_i^{DOE}$ 182. Process parameters, $PP_i^{DOE}$ 182, include process settings and conditions that vary over the duration of a wafer process (e.g., etch process). By defining the set of process dependent parameters and their values, process simulation module 181 effectively reduces the parameter space explored by DOE profile generation module 161. Process independent geometric parameters, $PIP_k^{DOE}$ 184, are not affected by the process and their values are linked (e.g., fixed) for the duration of the process.

DOE profile generation module 161 receives process dependent geometric parameter values, $PDP_j^{DOE}$ 183, and process independent geometric parameters, $PIP_k^{DOE}$ 184, and generates a set of DOE shape profiles 185 associated with each value of one or more parameters of interest $POI_j^{DOE}$ 187. The set of DOE shape profiles 185 is significantly smaller than the set of DOE shape profiles 163 described with reference to FIG. 3 due to the constraining effect of process simulation module 181 on the parameter space explored by DOE profile generation module 161.

Metrology simulation module 162 generates a set of spectral signals 186 associated with a simulated measurement of each corresponding DOE shape profile 185 by metrology system 101. In some embodiments, the spectral signals 186 are reduced by a transformation model in the manner described with reference to FIG. 2. In the example depicted in FIG. 5, spectral signals 186 are employed directly for measurement model training.

As depicted in FIG. 5, measurement model training module 152 generates a trained measurement model 158 based on reduced spectral signals 186 and corresponding values of the one or more parameters of interest 187 in the manner described with reference to FIG. 2. Trained measurement model 158 is communicated from process control metrology model training engine 180 to a memory (e.g., memory 132), where it is stored.

In another further aspect, a SRM measurement model trained based on synthetic measurement data is further optimized based on actual measured spectra and corresponding reference measurement data as described with reference to FIG. 2. In some examples, a trained SRM measurement model is further optimized (e.g., measurement model parameters are tuned) to minimize precision errors, repeatability errors, DOE tracking errors, chamber to chamber mismatch, etc.

In another aspect, computing system 130 is configured as a process control metrology engine to directly estimate values of one or more parameters of interest based on spectral measurements of wafers under process using a trained measurement model.

Figure 6:
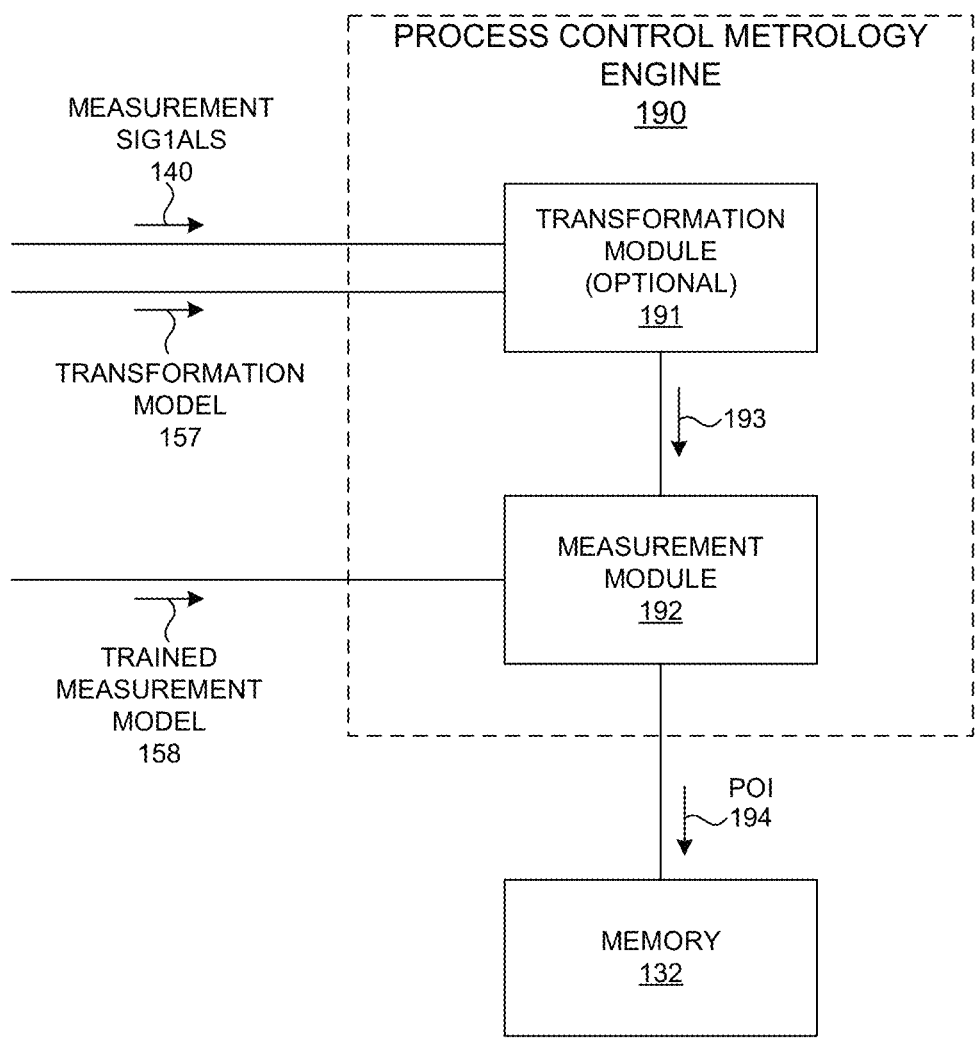
FIG. 6 is a diagram illustrative of an exemplary process control metrology engine 190 in one embodiment.

FIG. 6 is a diagram illustrative of an exemplary process control metrology engine 190 in one embodiment. As depicted in FIG. 6, process control metrology engine 190 includes a transformation module 191 and measurement module 192. As depicted in FIG. 6, transformation module 191 employs transformation model 157, described with reference to FIG. 2, to transform actual measurement signals (e.g., signals 140) to a reduced set of measurement signals 193. Transformation model 157 was generated based on DOE measurements of particular structures by a particular metrology system (e.g., metrology system 101). As depicted in FIG. 6, transformation model 157 is applied to actual measurements of the same nominal structure by the same nominal metrology system (e.g., metrology system 101). The reduced set of measurement signals 193 are communicated to measurement module 192. Measurement module 192 employs trained SRM measurement model 158, described with reference to FIGS. 2-5, to directly estimate values of parameters of interest, POI 194, (e.g., etch depth). The estimated values are communicated to a memory (e.g., memory 132), and stored.

In another aspect, a trained signal decontamination model is employed to generate decontaminated optical spectra from measured optical spectra while the wafer is being processed. The decontaminated spectra are employed to determine values of parameters of interest by physical model based regression, library regression, or an SRM measurement model as described herein. The parameters of interest are provided as feedback to control the process tool.

A signal decontamination model is trained based on optical spectra collected from one or more Design of Experiments (DOE) wafers by the process tool. The DOE wafers include variations of critical and non-critical structural parameters, etch process conditions and settings, wafers fabricated in different etch chambers, etc. Values of parameters of interest associated with the DOE wafers are estimated by measurement by a reference metrology tool, either by direct measurement or by interpolation as described herein. Furthermore, decontaminated spectra are simulated based on the measured values of the parameters of interest. The measured spectra and the decontaminated spectra are employed to train the signal decontamination model. The trained signal decontamination model provides a transfer function from measured spectral signals to decontaminated spectra useable to estimate values of one or more parameters of interest.

In general, the trained decontamination isolates spectral variations induced by variations of one or more parameters of interest from spectral variations induced by variations of other parameters or sources of measurement noise. For example, the measurement spot associated with metrology system 101 is generally quite large due to the large distance that must be maintained between the optical components and the wafer. For this reason, a spectral measurement performed by metrology system 101 includes desirable signal information from a metrology target of interest that lies within the measurement spot and a significant amount of undesirable signal information from areas surrounding the metrology target within the measurement spot. Signal information from areas surrounding the metrology target is undesirable because a physically based model of the entire measurement spot is computationally impractical, if not intractable. A trained signal decontamination model effectively maps measured spectra associated with the entire measurement spot to spectra associated with a portion of the wafer that can be physically modelled.

In some embodiments, computing system 130 is configured as a signal decontamination model training engine to train a signal decontamination model employed to generate decontaminated spectra based on spectral measurements of structures under process.

Figure 7:
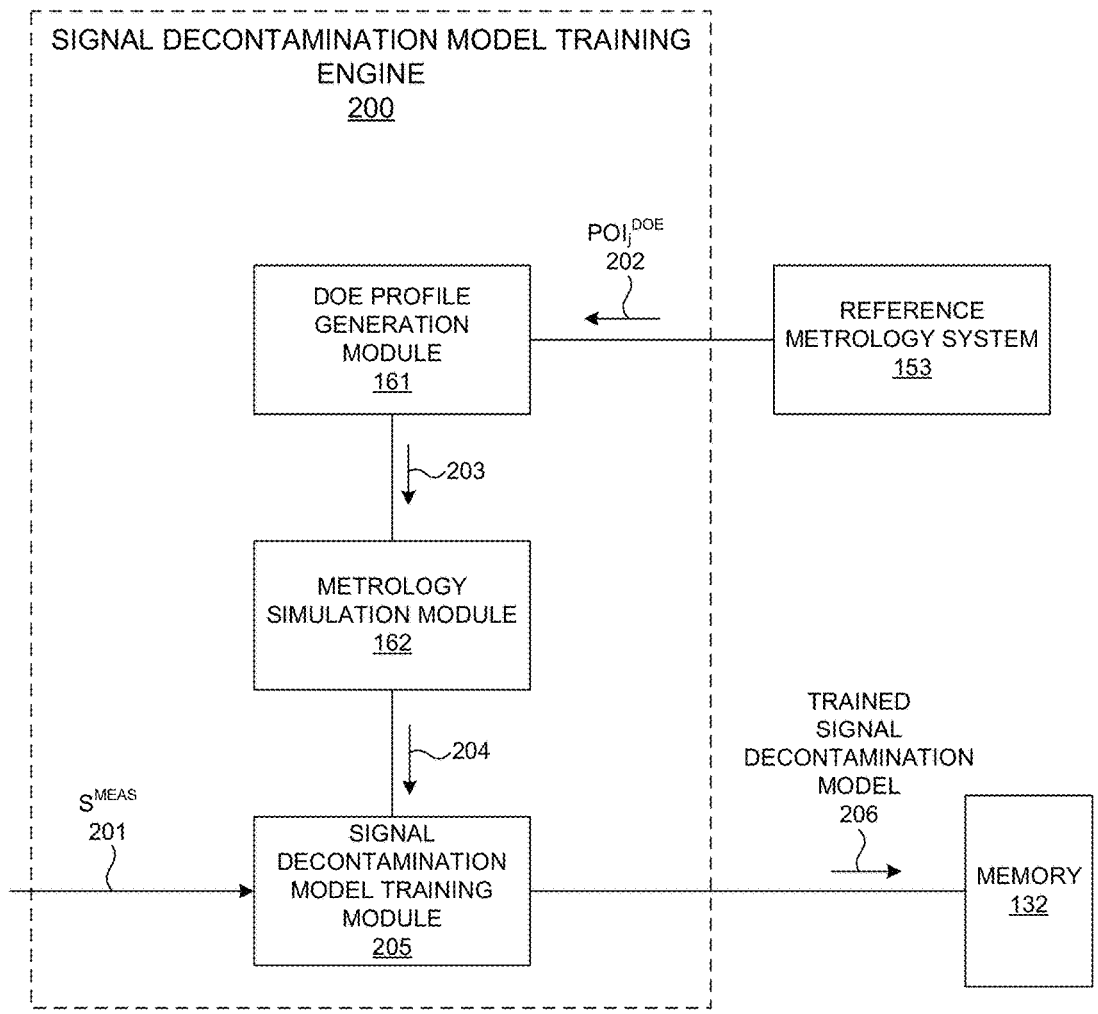
FIG. 7 is a diagram illustrative of an exemplary signal decontamination model training engine 200 in one embodiment.

FIG. 7 is a diagram illustrative of an exemplary signal decontamination model training engine 200 in one embodiment. In the depicted embodiment, signal decontamination model training engine 200 includes a DOE profile generation module 161, a metrology simulation module 162 as described with reference to FIGS. 3-5. In addition, signal decontamination model training engine 200 includes signal decontamination model training module 205.

As depicted in FIG. 7, a set of DOE wafers are measured by a metrology system, such as metrology system 101 of wafer processing system 100. The measured spectral signals, $S^{MEAS}$ 201, are provided to signal decontamination model training module 205. The same set of DOE wafers are measured by a reference metrology system 153 as described hereinbefore. The measured values of one or more parameters of interest, $POI_j^{DOE}$ 202, are provided to DOE profile generation module 161.

DOE profile generation module 161 generates a set of DOE shape profiles 203 corresponding to each different value of the one or more parameters of interest, $POI_j^{DOE}$ 202, while values of other parameters necessary to describe the DOE profile (e.g., sidewall angle, CD, etc.) are maintained at nominal values.

Metrology simulation module 162 generates a set of spectral signals 204 associated with a simulated measurement of each corresponding DOE shape profile 203 by metrology system 101. As depicted in FIG. 7, signal decontamination model training module 205 generates a trained signal decontamination model 206 based on simulated spectral signals 204 and corresponding actual measured spectral signals 201. At each step, each measured spectral signals 201 and corresponding simulated spectral signals 204 share the same value of one or more parameters of interest, e.g., etch depth. Trained signal decontamination model 206 is communicated from signal decontamination model training engine 200 to a memory (e.g., memory 132), where it is stored.

In general, any signal decontamination model described herein is implemented as a neural network model. In other examples, any signal decontamination model may be implemented as a linear model, a non-linear model, a polynomial model, a response surface model, a support vector machines model, a random forest model, a deep network model, a convolutional network model, or other types of models. In some examples, any trained signal decontamination model described herein may be implemented as a combination of models.

In another aspect, computing system 130 is configured as a signal decontamination engine to directly generate decontaminated spectra based on spectral measurements of wafers under process using a trained signal decontamination model.

Figure 8:
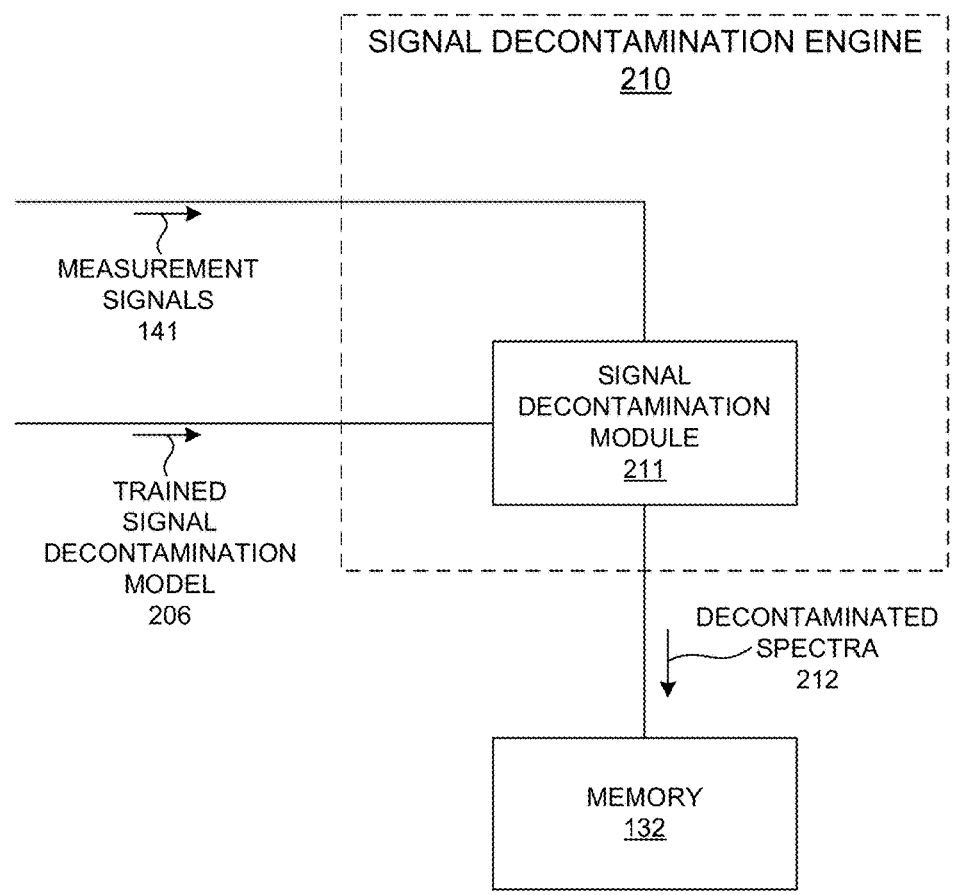
FIG. 8 is a diagram illustrative of an exemplary signal decontamination engine 210 in one embodiment.

FIG. 8 is a diagram illustrative of an exemplary signal decontamination engine 210 in one embodiment. As depicted in FIG. 8, signal decontamination engine 210 includes a signal decontamination module 211. As depicted in FIG. 8, signal decontamination module 211 employs trained signal decontamination model 206, described with reference to FIG. 7, to transform actual spectral measurement signals (e.g., signals 140) to a decontaminated set of spectral measurement signals 212. The decontaminated spectral measurement signals 212 are communicated to a memory (e.g., memory 132), and stored.

In a further aspect, values of one or more parameters of interest are determined based on decontaminated measurement signals 212 using a physical model based regression (e.g., regression with an optical system simulator), library based regression, or a trained SRM measurement model as described herein.

The signal decontamination model effectively transforms raw spectra collected by one optical subsystem into spectra associated with a simulated optical subsystem. The decontaminated spectra contain signal information associated with critical parameters with minimal signal information associated with measurement noise, signal contamination from undesirable measurement areas, and variations of other non-critical parameters.

Figure 9:
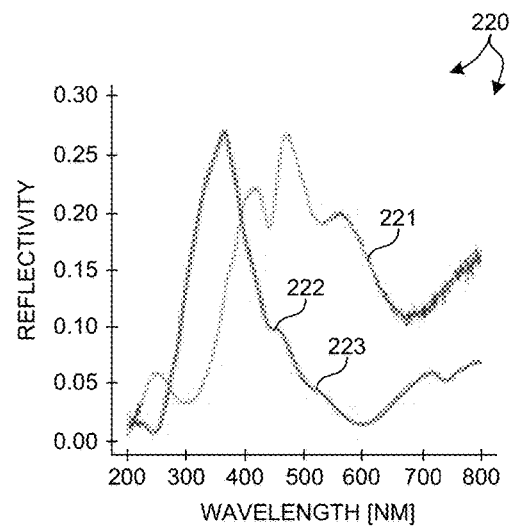
FIG. 9 depicts a plot 220 illustrative of a reduction in signal noise by operation of a signal decontamination model on a measured spectrum.

FIG. 9 depicts a plot 220 illustrative of a reduction in signal noise by operation of a signal decontamination model on a measured spectrum. Plotline 221 depicts a measured reflectivity signal associated with an in-situ spectral reflectometry measurement of a periodic fin structure characterized by a height parameter and surrounding area. Plotline 222 depicts a simulated reflectivity measurement signal associated an in-situ spectral reflectometry measurement of the periodic fin structure isolating signal information associated with the parameter of interest (i.e., the height parameter). Plotline 223 depicts a decontaminated signal 223 generated by transforming the measured reflectivity signal 221 with a trained signal decontamination model. As depicted in FIG. 9, the raw measured reflectivity signal 221 is noisy, while the decontaminated signal 223 is significantly less noisy. Also, the fit between the simulated reflectivity measurement signal 222 and the decontaminated signal 223 is very good as the signals nearly overlap in plot 220.

Figure 10:
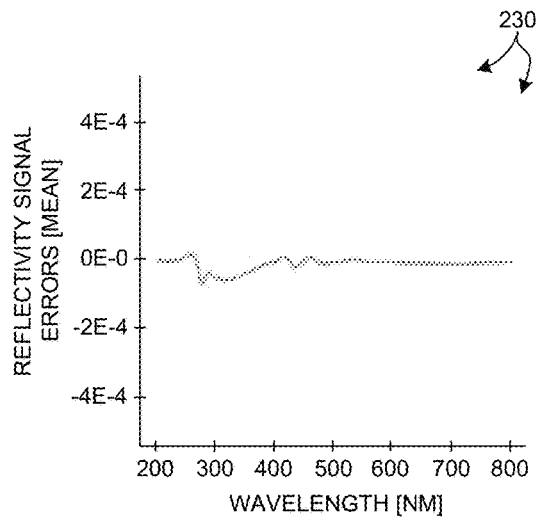
FIG. 10 depicts a plot 230 illustrative of the mean values of the reflectivity signal errors associated with simulated reflectivity measurement signals and decontaminated signals for multiple spectra.

FIG. 10 depicts a plot 230 illustrative of the mean values of the reflectivity signal errors (i.e., difference) between simulated reflectivity measurement signals and decontaminated signals associated with multiple spectra.

Figure 11:
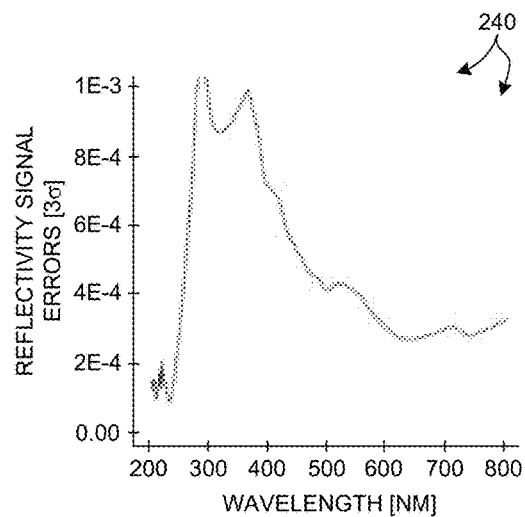
FIG. 11 depicts a plot 240 illustrative of the three sigma values of the reflectivity signal errors associated with simulated reflectivity measurement signals and decontaminated signals for multiple spectra.

FIG. 11 depicts a plot 240 illustrative of the three sigma values of the reflectivity signal errors (i.e., difference) between simulated reflectivity measurement signals and decontaminated signals associated with multiple spectra. As illustrated in FIGS. 9-11, the reflectivity signal errors are within the noise level of the raw spectra provided to the signal decontamination model.

In some embodiments, the transformation model 157 described herein is a signal decontamination model as described herein.

In another aspect, one or more metrology systems integrated with a process tool are configured to measure multiple, different areas of a wafer during a process interval. Estimated values of one or more parameters of interest are determined using a trained SRM measurement model, a trained signal decontamination model, or both, as described herein. In some embodiments, a wafer uniformity value associated with each measured parameter of interest is determined based on measured values of each parameter of interest across the wafer. In some embodiments, a wafer uniformity value associated with each measured parameter of interest is determined based on measured spectra at multiple, different areas across the wafer. In these embodiments, a trained SRM measurement model determines the wafer uniformity value associated with each measured parameter of interest based on the measured spectra at multiple, different areas across the wafer.

In some embodiments, multiple metrology systems are integrated with the process tool and the metrology systems are configured to simultaneously measure different areas across the wafer during process. In some embodiments, a single metrology system integrated with a process tool is configured to sequentially measure multiple, different areas of a wafer during process.

In some embodiments, different areas of the wafer under process include metrology targets having different structures. In these embodiments, a SRM measurement model, a signal decontamination model, or both, are configured as multiple target models (i.e., training and measurement during process are performed on multi-target spectra). In one example, a multi-target spectra is a vector of spectra each associated with a different metrology target located at a different area on the wafer (e.g., $S=[S_1, S_2, \ldots, S_m]$).

In a further aspect, the determination of values of one of more parameters of interest at a particular time during a process interval involves values of one or more parameters determined by external reference metrology or in-situ metrology at a previous step of the process.

In yet another further aspect, the measurement results described herein can be used to provide active feedback to the process tool (e.g., lithography tool, etch tool, deposition tool, etc.). For example, values of measured parameters determined based on measurement methods described herein can be communicated to an etch tool to adjust the etch time to achieve a desired etch depth. In a similar way etch parameters (e.g., etch time, diffusivity, etc.) or deposition parameters (e.g., time, concentration, etc.) may be included in a measurement model to provide active feedback to etch tools or deposition tools, respectively. In some example, corrections to process parameters determined based on measured device parameter values and a trained measurement model may be communicated to the process tool. In one embodiment, computing system 130 determines values of one or more parameters of interest during process based on measured signals 141 received from metrology system 101. In addition, computing system 130 communicates control commands 142 to process controller 143 based on the determined values of the one or more parameters of interest. The control commands 142 cause the process controller 143 to change the state of the ongoing process (e.g., stop the etch process, change the diffusivity, etc.). In one example, control command 142 causes process controller 143 to stop the etch process when a desired etch depth is measured. In another example, control command 142 causes process controller 143 to change etch rate to improve measured wafer uniformity of a CD parameter.

Although a metrology system 101 depicted in FIG. 1 is a spectral reflectometry system, any number of different metrology systems or combinations of different metrology systems may be integrated with a process system and used to measure parameters of interest during process in accordance with the methods described herein.

In some embodiments, the methods and systems for in-situ spectral reflectometry metrology of semiconductor devices undergoing a process as described herein are applied to the measurement of memory structures. These embodiments enable optical critical dimension (CD), film, and composition metrology for periodic and planar structures.

In some examples, the measurement models are implemented as an element of a SpectraShape® optical critical-dimension metrology system available from KLA-Tencor Corporation, Milpitas, Calif., USA. In this manner, the model is created and ready for use immediately after the spectra are collected by the system.

In some other examples, the measurement models are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

Figure 12:
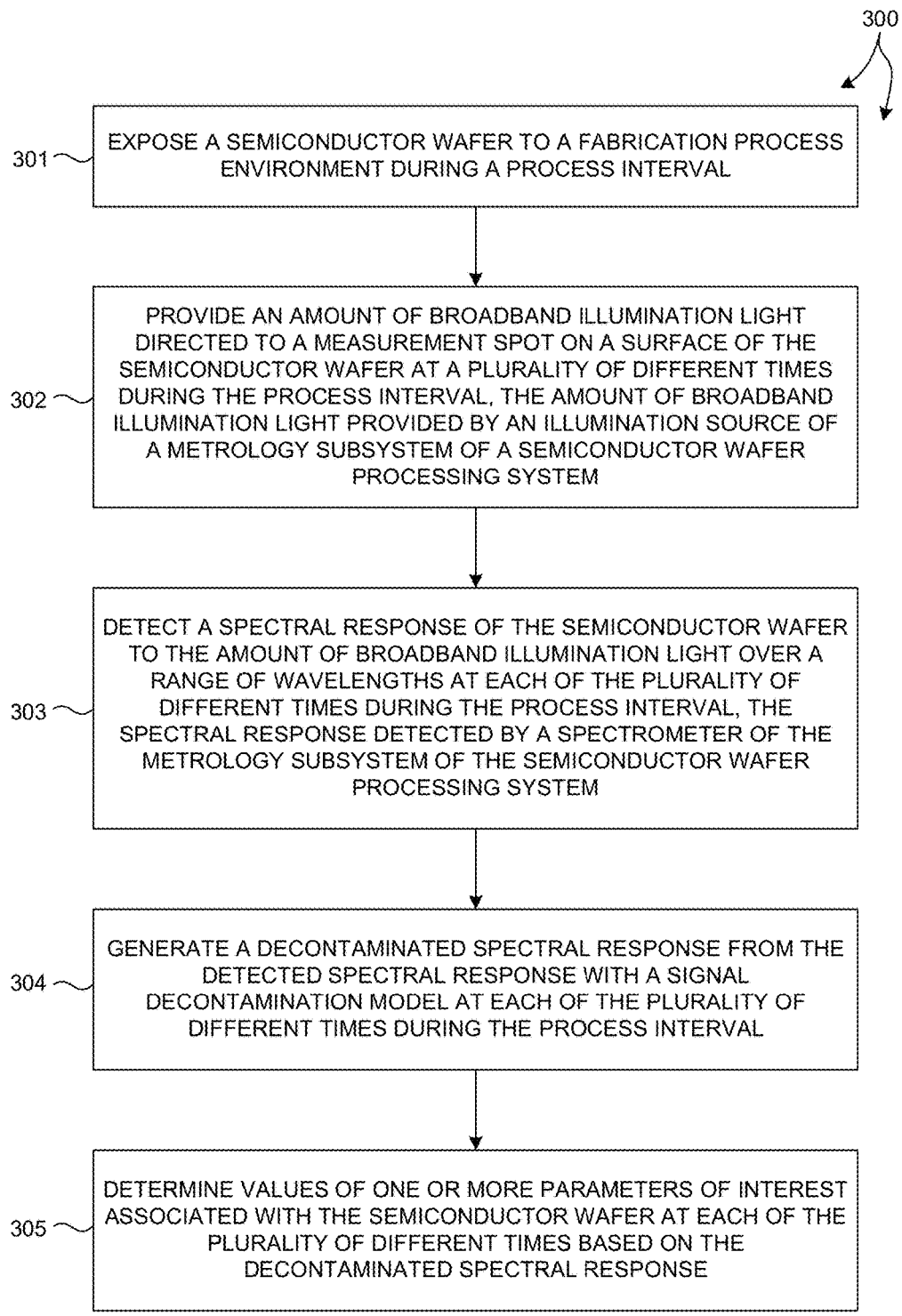
FIG. 12 illustrates a flowchart of a method 300 for estimating values of parameters of interest from measurements of structures on a wafer while the wafer is under process.

FIG. 12 illustrates a method 300 of performing metrology measurements during process in at least one novel aspect. Method 300 is suitable for implementation by a wafer processing system such as wafer processing system 100 illustrated in FIG. 1 of the present invention. In one aspect, it is recognized that data processing blocks of method 300 may be carried out via a pre-programmed algorithm executed by one or more processors of computing system 130, or any other general purpose computing system. It is recognized herein that the particular structural aspects of metrology system 100 do not represent limitations and should be interpreted as illustrative only.

In block 301, a semiconductor wafer is exposed to a fabrication process environment during a process interval.

In block 302, an amount of broadband illumination light is provided to a measurement spot on a surface of the semiconductor wafer at a plurality of different times during the process interval. The amount of broadband illumination light is provided by an illumination source of a metrology subsystem of a semiconductor wafer processing system.

In block 303, a spectral response of the semiconductor wafer to the amount of broadband illumination light is detected over a range of wavelengths at each of the plurality of different times during the process interval. The spectral response is detected by a spectrometer of the metrology subsystem of the semiconductor wafer processing system.

In block 304, a decontaminated spectral response is generated from the detected spectral response using a signal decontamination model at each of the plurality of different times during the process interval.

In block 305, values of one or more parameters of interest associated with the semiconductor wafer at each of the plurality of different times are determined based on the decontaminated spectral response.

In a further embodiment, system 100 includes one or more computing systems 130 employed to perform measurements of semiconductor structures based on spectroscopic measurement data collected in accordance with the methods described herein. The one or more computing systems 130 may be communicatively coupled to one or more spectrometers, active optical elements, process controllers, etc. In one aspect, the one or more computing systems 130 are configured to receive measurement data associated with spectral measurements of structures of wafer 104.

It should be recognized that one or more steps described throughout the present disclosure may be carried out by a single computer system 130 or, alternatively, a multiple computer system 130. Moreover, different subsystems of system 100 may include a computer system suitable for carrying out at least a portion of the steps described herein. Therefore, the aforementioned description should not be interpreted as a limitation on the present invention but merely an illustration.

In addition, the computer system 130 may be communicatively coupled to the spectrometers in any manner known in the art. For example, the one or more computing systems 130 may be coupled to computing systems associated with the spectrometers. In another example, the spectrometers may be controlled directly by a single computer system coupled to computer system 130.

The computer system 130 of system 100 may be configured to receive and/or acquire data or information from the subsystems of the system (e.g., spectrometers and the like) by a transmission medium that may include wireline and/or wireless portions. In this manner, the transmission medium may serve as a data link between the computer system 130 and other subsystems of system 100.

Computer system 130 of system 100 may be configured to receive and/or acquire data or information (e.g., measurement results, modeling inputs, modeling results, reference measurement results, etc.) from other systems by a transmission medium that may include wireline and/or wireless portions. In this manner, the transmission medium may serve as a data link between the computer system 130 and other systems (e.g., memory on-board system 100, external memory, or other external systems). For example, the computing system 130 may be configured to receive measurement data from a storage medium (i.e., memory 132 or an external memory) via a data link. For instance, spectral results obtained using the spectrometers described herein may be stored in a permanent or semi-permanent memory device (e.g., memory 132 or an external memory). In this regard, the spectral results may be imported from on-board memory or from an external memory system. Moreover, the computer system 130 may send data to other systems via a transmission medium. For instance, a measurement model or an estimated parameter value determined by computer system 130 may be communicated and stored in an external memory. In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 1, program instructions 134 stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the system 100 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor measurement system that may be used for measuring a specimen within any semiconductor processing tool (e.g., an inspection system or a lithography system). The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A semiconductor wafer processing system comprising:
a semiconductor fabrication process chamber comprising a fabrication process environment;
  a semiconductor wafer disposed inside the fabrication process chamber and exposed to the fabrication process environment during a process interval; a metrology subsystem comprising:
  an illumination source configured to provide an amount of broadband illumination light directed to a measurement spot on a surface of the semiconductor wafer at a plurality of different times during the process interval;
  a spectrometer configured to collect an amount of reflected light from the semiconductor wafer and detect a spectral response of the semiconductor wafer to the amount of broadband illumination light over a range of wavelengths at each of the plurality of different times during the process interval;
  an optical subsystem configured to direct the amount of broadband illumination light from the illumination source to the measurement spot on the surface of the semiconductor wafer during the process interval and direct the amount of light reflected from the measurement spot on the surface of the semiconductor wafer toward the spectrometer; and
  a computing system configured to:
  generate a decontaminated spectral response from the detected spectral response with a signal decontamination model at each of the plurality of different times during the process interval, determine values of one or more parameters of interest associated with the semiconductor wafer at each of the plurality of different times based on the decontaminated spectral response using a trained signal response metrology (SRM) measurement model that functionally relates the decontaminated spectral response of the semiconductor wafer to the values of the one or more parameters of interest at each of the plurality of different times or a regression of a physically based measurement model at each of the plurality of different times.

2. The semiconductor wafer processing system of claim 1, the computing system further configured to generate a process control command based on the determined values of the one or more parameters of interest at one or more of the plurality of different times, wherein the process control command causes a change of the fabrication process environment.

3. The semiconductor wafer processing system of claim 1, wherein the computing system is further configured to train the SRM measurement model based on Design of Experiments (DOE) values of the one or more parameters of interest and corresponding DOE spectra at a second plurality of different times within the process interval.

4. The semiconductor wafer processing system of claim 3, wherein the DOE values of the one or more parameters of interest are estimated based on measurements by a reference metrology system different from the metrology subsystem system and the corresponding DOE spectra are measured by the metrology subsystem.

5. The semiconductor wafer processing system of claim 4, wherein the DOE values of the one or more parameters of interest at one or more of the second plurality of different times within the process interval are interpolated from measurements by the reference metrology system at a different time of the process interval.

6. The semiconductor wafer processing system of claim 3, wherein the DOE values of the one or more parameters of interest at the second plurality of different times within the process interval are programmed and the corresponding DOE spectra are generated by a simulation based on the programmed DOE values.

7. The semiconductor wafer processing system of claim 6, wherein one or more parameters of the simulation are constrained based on a parameter correlation function.

8. The semiconductor wafer processing system of claim 6, wherein one or more parameters of the simulation are constrained to a set of values of the one or more parameters based on a process simulation.

9. The semiconductor wafer processing system of claim 1, wherein the fabrication process environment is an etch process environment or a deposition process environment.

10. The semiconductor wafer processing system of claim 1 wherein the trained SRM measurement model is any of a neural network model, a linear model, a non-linear model, a polynomial model, a response surface model, a support vector machines model, a decision tree model, a random forest model, a deep network model, and a convolutional network model.

11. The semiconductor wafer processing system of claim 1, wherein the determining of the values of the one or more parameters of interest at a time within the process interval is based on the spectral response of the semiconductor wafer at the time within the process interval and one or more prior times within the process interval.

12. The semiconductor wafer processing system of claim 1, wherein the metrology subsystem is a spectroscopic reflectometer.

13. The semiconductor wafer processing system of claim 1, wherein the metrology subsystem is configured to measure multiple, different locations on the semiconductor wafer, and wherein the computing system is further configured to determine a value of a wafer uniformity metric based on the values of the one or more parameters of interest associated with each of the multiple, different locations.

14. The semiconductor wafer processing system of claim 1, wherein the signal decontamination model removes signal information from the detected spectral response that is associated with parameters different from the one or more parameters of interest.

15. A semiconductor wafer processing system comprising:
  a semiconductor fabrication process chamber comprising a fabrication process environment;

a semiconductor wafer disposed inside the fabrication process chamber and exposed to the fabrication process environment during a process interval;

a metrology subsystem comprising:
an illumination source configured to provide an amount of broadband illumination light directed to a measurement spot on a surface of the semiconductor wafer at a plurality of different times during the process interval;
a spectrometer configured to collect an amount of reflected light from the semiconductor wafer and detect a spectral response of the semiconductor wafer to the amount of broadband illumination light over a range of wavelengths at each of the plurality of different times during the process interval;
an optical subsystem configured to direct the amount of broadband illumination light from the illumination source to the measurement spot on the surface of the semiconductor wafer during the process interval and direct the amount of light reflected from the measurement spot on the surface of the semiconductor wafer toward the spectrometer; and
a computing system configured to:
generate a decontaminated spectral response from the detected spectral response with a signal decontamination model at each of the plurality of different times during the process interval; and
determine values of one or more parameters of interest associated with the semiconductor wafer at each of the plurality of different times based on the decontaminated spectral response.

16. The semiconductor wafer processing system of claim 15, wherein the determining of the values of the one or more parameters of interest based on the decontaminated spectral response involves a trained signal response metrology (SRM) measurement model or a regression of a physically based measurement model.

17. The semiconductor wafer processing system of claim 15, the computing system further configured to generate a process control command based on the determined values of the one or more parameters of interest at one or more of the plurality of different times, wherein the process control command causes a change of the fabrication process environment.

18. The semiconductor wafer processing system of claim 15, wherein the computing system is further configured to train the signal decontamination model based on Design of Experiments (DOE) values of the one or more parameters of interest measured by a reference metrology system and corresponding DOE spectra measured by the metrology subsystem.

19. A method comprising:
exposing a semiconductor wafer to a fabrication process environment during a process interval;
providing an amount of broadband illumination light directed to a measurement spot on a surface of the semiconductor wafer at a plurality of different times during the process interval, the amount of broadband illumination light provided by an illumination source of a metrology subsystem of a semiconductor wafer processing system;
detecting a spectral response of the semiconductor wafer to the amount of broadband illumination light over a range of wavelengths at each of the plurality of different times during the process interval, the spectral response detected by a spectrometer of the metrology subsystem of the semiconductor wafer processing system;
generating a decontaminated spectral response from the detected spectral response with a signal decontamination model at each of the plurality of different times during the process interval; and
determining values of one or more parameters of interest associated with the semiconductor wafer at each of the plurality of different times based on the decontaminated spectral response.

20. The method of claim 19, further comprising:
training the signal decontamination model based on Design of Experiments (DOE) values of the one or more parameters of interest measured by a reference metrology system and corresponding DOE spectra measured by the metrology subsystem, wherein the training involves:
determining a set of DOE shape profiles corresponding to each of the DOE values of the one or more parameters of interest, wherein values of other parameters necessary to define the DOE profile are maintained at nominal values;
determining a set of simulated spectral signals associated with a simulated measurement of each DOE shape profile by the metrology subsystem; and
training the signal decontamination model based on the simulated spectral signals and the corresponding DOE spectra measured by the metrology subsystem.

21. The method of claim 19, further comprising:
generating a process control command based on the determined values of the one or more parameters of interest at one or more of the plurality of different times, wherein the process control command causes a change of the fabrication process environment.

22. The method of claim 19, wherein the determining of the values of the one or more parameters of interest involves a trained signal response metrology (SRM) measurement model that functionally relates the decontaminated spectral response of the semiconductor wafer to the values of the one or more parameters of interest at each of the plurality of different times during the process interval.

23. The method of claim 20, wherein the DOE values of the one or more parameters of interest are interpolated from measurements by the reference metrology system.

24. The method of claim 19, wherein the fabrication process environment is an etch process environment or a deposition process environment.

25. The method of claim 19, wherein the determining of the values of the one or more parameters of interest at a time within the process interval is based on the decontaminated spectral response of the semiconductor wafer at the time within the process interval and one or more prior times within the process interval.

* * * * *